US00PP31502P3

(12) United States Plant Patent
Gray et al.

(10) Patent No.: US PP31,502 P3
(45) Date of Patent: Mar. 3, 2020

(54) FLORIBUNDA ROSE PLANT NAMED 'GRATUSC'

(50) Latin Name: ***Rosa* hybrid**
Varietal Denomination: GRAtusc

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 16/350,971

(22) Filed: Feb. 6, 2019

(65) Prior Publication Data

US 2019/0246534 P1 Aug. 8, 2019

Related U.S. Application Data

(60) Provisional application No. 62/626,802, filed on Feb. 6, 2018.

(51) Int. Cl.
*A01H 5/02* (2018.01)
*A01H 6/74* (2018.01)

(52) U.S. Cl.
USPC ..... Plt./147
CPC ..... *A01H 6/749* (2018.05)

(58) Field of Classification Search
USPC ..... Plt./147
CPC ..... A01H 5/02; A01H 6/74
See application file for complete search history.

*Primary Examiner* — Annette H Para
(74) *Attorney, Agent, or Firm* — Samuel R. McCoy, Jr.

(57) ABSTRACT

'GRAtusc' is a new and distinct floribunda type *Rosa* hybrid cultivar which is characterized by the combination of an upright to semi-weeping, bushy growth habit, nearly continuous flowering, with flowers that exhibit a distinct pink blended yellow color becoming terracotta with summer heat and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAtusc'.

BACKGROUND OF THE INVENTION

Parentage: 'GRAtusc' is a seedling selection which resulted from the controlled cross-pollination of an unnamed *Rosa* hybrid female breeding line (not patented) and an unnamed *Rosa* hybrid male breeding line (not patented). Both parents, developed by the same inventor and never commercially released, exhibited traits deemed commercially significant and desirable.

After many years of trialing, the female parent was confirmed to possess a combination of desirable traits such as very strong fragrance and having flower color white, borne on a bushy plant growing to 1.2 m tall and wide. The male parent was selected for use in breeding after trialing confirmed the presence of a modern flower color. During the spring of 2013, the female parent was emasculated and was manually pollinated with pollen from the male parent. In autumn of 2014, seed was collected from hips produced by the female parent and a number of seedlings were grown to a mature size, including the claimed plant. These progeny were further evaluated for desirable traits such as black spot disease resistance and original flower color, and in January of 2015 the claimed plant was first observed. In January of 2017, after further evaluation for desirable traits, the claimed plant was deemed to be garden-worthy and suited to widespread cultivation. It was given the denomination 'GRAtusc'.

Asexual Reproduction: Asexual propagation of 'GRAtusc', by way of softwood stem cuttings, was first performed in September of 2015 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAtusc'. These traits, in combination, distinguish 'GRAtusc' as a new and distinct cultivar.

1. *Rosa* hybrid 'GRAtusc' exhibits an upright to semi-weeping growth habit; and
2. *Rosa* hybrid 'GRAtusc' flowers exhibit pink blended yellow flowers becoming terracotta color with summer heat; and
3. *Rosa* hybrid 'GRAtusc' exhibits nearly continuous flowering; and
4. *Rosa* hybrid 'GRAtusc' exhibits a double flower type.

DETAILED BOTANICAL DESCRIPTION

Figure 1:
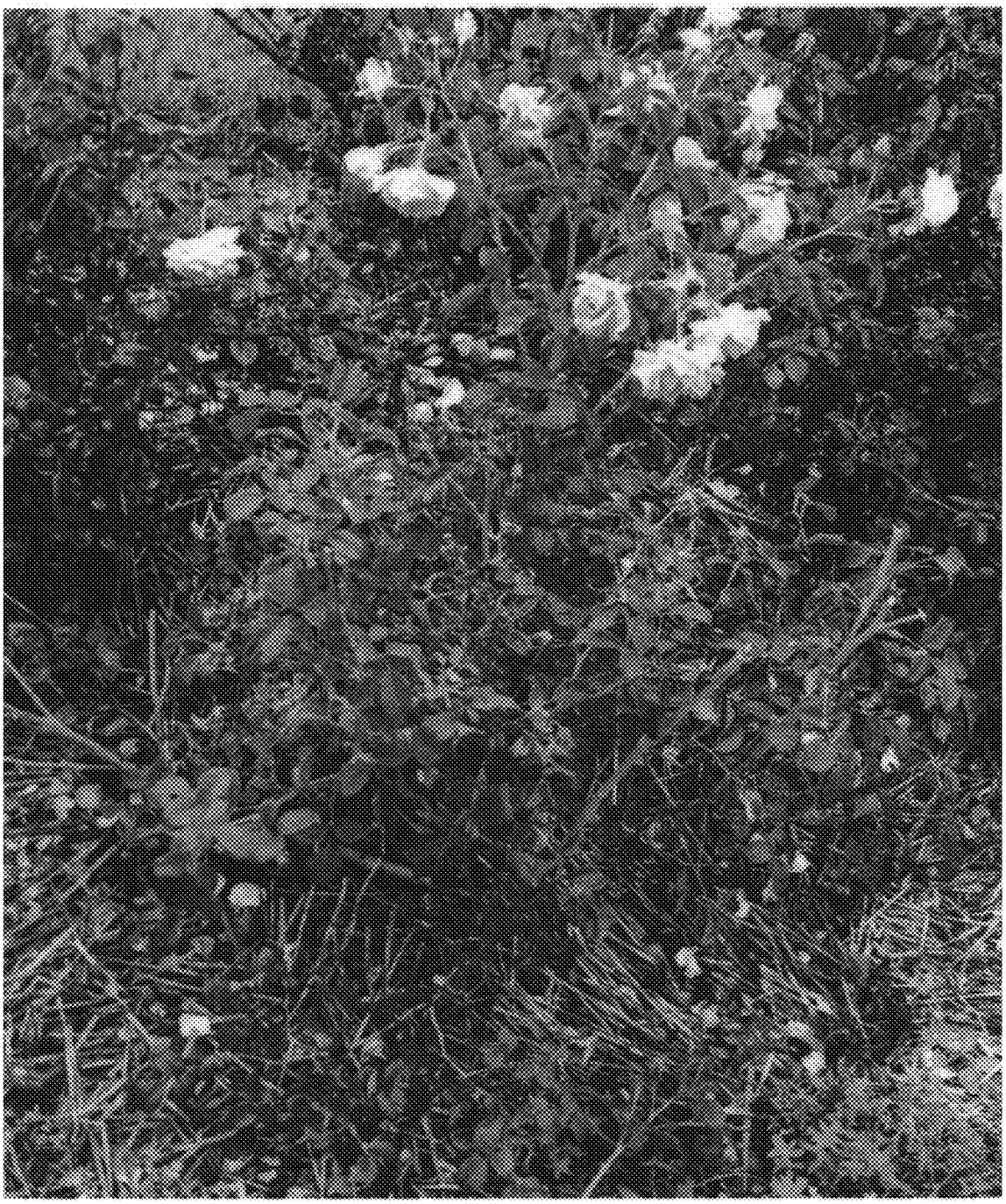
FIG. 1 illustrates, as nearly true as it is reasonably possible to make the same in color photographs of this type, an exemplary 6 month old 'GRAtusc' plant grown outdoors at the inventor's commercial nursery in Highfields, Australia.
Figure 2:
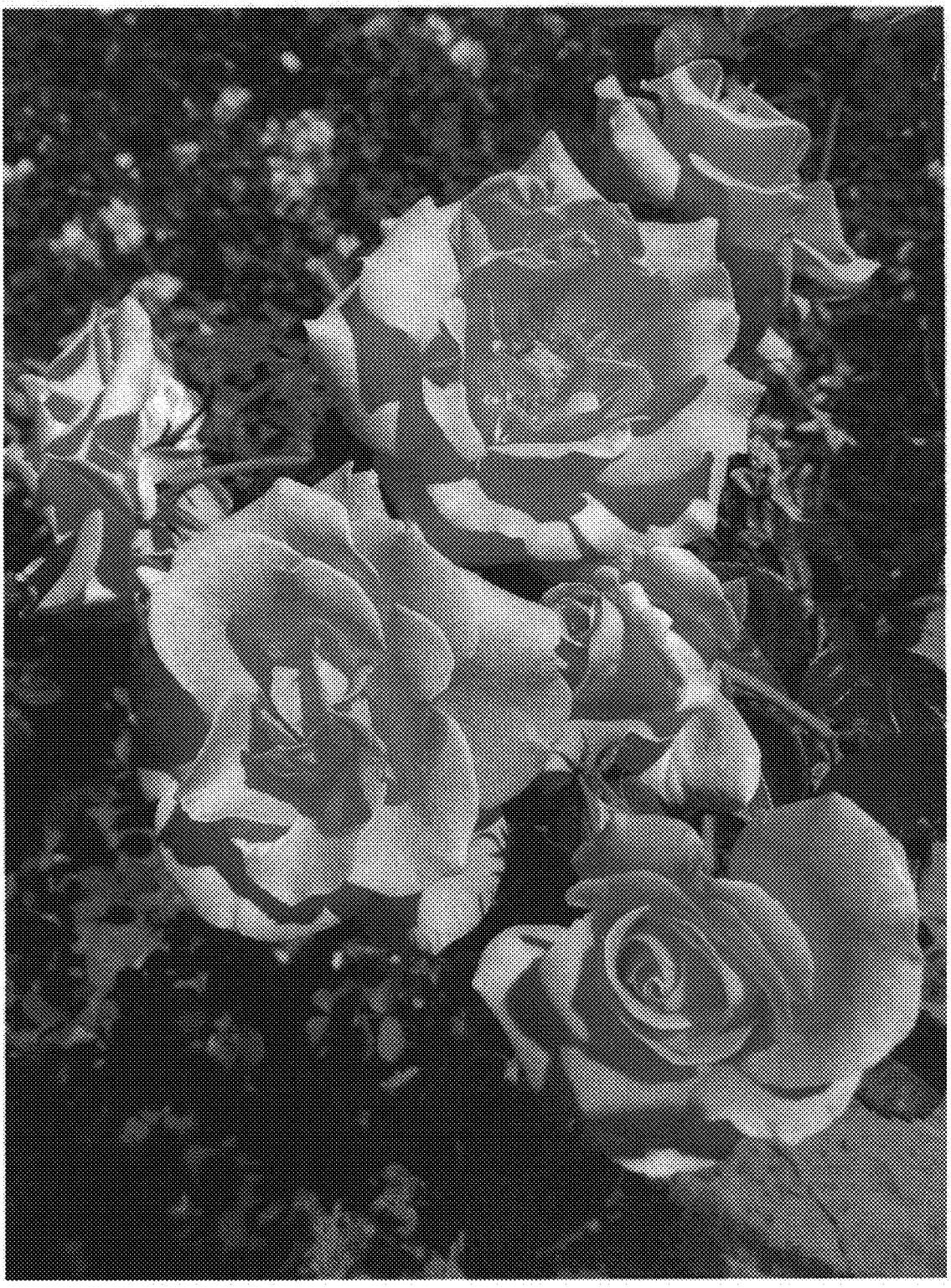
FIG. 2 illustrates, as nearly true as it is reasonably possible to make the same in color photographs of this type, the typical flower of 'GRAtusc'.

The following observations and measurements, made in January of 2018, describe averages of two own-root specimens of one year old 'GRAtusc' plants. The plants were grown outdoors in a garden bed of a red krasnozem soil in full sunlight, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAtusc' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2007 Fifth Edition except where common terms of color are used.

A botanical description of 'GRAtusc' and comparisons with the parents and the most similar commercial cultivar of *Rosa* hybrid are provided below.

General plant description:

*Growth habit*.—Upright to semi-weeping.

*Growth rate*.—Approximately 8 months to reach 40 cm.

*Dimensions*.—80 cm tall and 60 cm wide.

*Environmental tolerance*.—Very good heat tolerance; cold hardiness is unknown.

*Disease resistance*.—Excellent resistance to powdery mildew (*Sphaerotheca pannosa*) and excellent resistance blackspot (*Diplocarpon rosae*).

*Propagation*.—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost buds near the apex of each shoot.

*Quantity*.—Numerous.

*General dimensions*.—Approximately 60 cm long; 1.0 cm in diameter near the base and tapering to 0.4 cm.

*Immature branches*.—Diameter — Approximately 0.5 cm. Texture and pubescence — Smooth with prickles; glabrous. Color — Near RHS 142C with no anthocyanin present. Prickles — Density — Sparse to moderate. Color — Near RHS 149C. Shape — Convex. Texture — Smooth.

*Mature branches*.—Diameter — Approximately 0.8 cm, after one year. Texture and pubescence — Smooth with prickles; glabrous. Color — Near RHS 149B. Prickles — Density — Sparse to moderate. Color — Near RHS 176A. Shape — Convex. Texture — Smooth.

Leaves:

*Arrangement*.—Alternate imparipinnate compound leaves.

*Quantity*.—Approximately 10 per mature branch.

*Attachment*.—Petiolate.

*Leaf internode length*.—2.0 cm.

*Dimensions*.—Approximately 10 cm long and 6 cm wide.

*Petiole*.—Dimensions — 2 cm long and 0.1 cm wide. Color — Near RHS 144D and margined RHS 143A. Texture and pubescence — Smooth and pubescent.

*Prickles*.—Present.

*Stipitate glands*.—Not present.

*Stipule*.—Dimensions — 1.5 cm long and 0.4 cm wide. Color — Near RHS 141B. Texture and pubescence — Pubescent. Margins — Ciliate. Apex — Apiculate. Base — Winged.

*Prickles*.—Not present.

*Stipitate glands*.—Not present.

*Rachis*.—Dimensions — 1.6 cm long and 0.1 cm wide. Color — Near RHS 143A. Prickles — present. Stipitate glands — Not present.

*Leaflets*.—Quantity — Seven leaflets on axillary leaves. Dimensions — Average size of the terminal leaflet is 3.7 cm long and 2.5 cm wide. Shape — Ovate. Apex — Acuminate. Base — Ovate. Margins — Serrated. Texture, pubescence and luster, adaxial surface — Smooth, glabrous, and glossy. Texture, pubescence and luster, abaxial surface — Smooth, glabrous, and matte. Juvenile foliage color, adaxial surface — Near RHS 143AB, with no anthocyanin intonations. Juvenile foliage color, abaxial surface — Near RHS 143C, with no anthocyanin intonations. Mature foliage color, adaxial surface — Near RHS N134A. Mature foliage color, abaxial surface — Near RHS 137C. Venation — Pinnate. Venation color, adaxial surface — Near RHS 137, with midrib RHS 136C. Venation color, abaxial surface — Near RHS 138A, with midrib RHS 138C.

*Petiolule*.—Dimensions — 0.2 cm long and 0.1 cm wide. Color — Near RHS 144A with no anthocyanin intonations present. Prickles — Not present. Texture — Smooth.

Inflorescence:

*Inflorescence type*.—Flowers are clustered.

*Blooming habit*.—Almost continuous from October through June in the southern hemisphere.

*Time to flower*.—6 to 8 weeks for a new stem to mature and flowering begins to occur once a stem matures.

*Peduncle*.—Dimensions — 22 cm long and 14 cm in diameter. Color — Near RHS 145B with no anthocyanin present. Strength — Rigid. Texture and pubescence — Smooth and glabrous. Prickles — Not present.

Bud:

*Shape*.—Ovate.

*Size*.—2.0 cm long and 1.0 cm in diameter.

*Color*.—Near RHS 141D with no anthocyanin present.

Flower:

*Calyx*.—General — Comprised of five polysepalous sepals. Diameter of calyx — 0.5 cm. Sepals — Color, interior surface — RHS 145C. Color, exterior surface — RHS 145A with no anthocyanin. Dimensions — 2.0 cm long and 0.5 cm wide. Apex — Apiculate. Base — Flat at union with receptacle. Quantity — Five. Pubescence — Densely puberulent. Margins — Entire. Stipitate glands — Not present.

*Corolla*.—General shape of corolla — Cupped and irregularly-rounded with a tight outer whorl. Rate of opening — 6 days from bud to anthesis. Dimensions — Approximately 7 cm in diameter and 4 cm deep. Fragrance — Mild sweet scent. Lastingness — On the plant for 5 days after anthesis. Persistence — Self-cleaning. Petals — Petal count — Exhibits semi double flowers with approximately 25 petals under normal conditions. Petal arrangement — Irregularly rounded whorl at anthesis and aging to a loose whorl. Dimensions — 3 cm long and 2.5 cm wide. Petal shape — Obovate. Apex — Rounded. Base — Flattened, then obtuse. Petal reflex — Slightly reflexed at apex. Petal margin — Entire; slightly undulating. Texture — Soft. Aspect — Formal. Petal color, upon opening — Upper surface — Near RHS 37B with base near RHS 9C. Lower surface — Near RHS 11B. Petal color, at anthesis — Upper surface — Near RHS 43D with base 6C. Lower surface — Near RHS 6D. Fading — Near RHS 2D.

Reproductive organs:

*Stamens*.—Quantity — Approximately 50. Anthers — Shape — Narrow ovate. Length — 0.1 cm. Color — Near RHS 5A. Pollen — Many. Pollen Color — Near RHS 3A. Filaments — Color — Near RHS 7A. Length — Approximately 0.8 cm.

*Pistils*.—Quantity — Approximately 50. Length — Approximately 1.0 cm. Stigma — Shape — Ovate. Color — Near RHS 11B. Style — Length — Approximately 0.8 cm long. Color — Near RHS 18C.

*Ovary*.—Dimensions — 0.5 cm long and 0.3 cm wide. Color — Near RHS 3D.

*Receptacle*.—Shape — Pitcher-shaped. Dimensions — 0.5 cm high and 0.5 cm wide. Color — Near RHS 142D.

Hip and seed:

*Hip*.—Shape — Rounded. Dimensions — 1.0 cm long and 1.5 cm wide. Texture — Smooth. Color — Near RHS 146C.

*Seed*.—Shape — Rounded. Dimensions — 1.0 cm long and 1.0 cm wide. Color — Near RHS 144D.

Comparisons with the parents: The new rose plant 'GRAtusc' may be distinguished from its seed parent, an unnamed breeding line (not patented), by the following combination of characteristics: 1. The flowers of 'GRAtusc' exhibit a distinct pink blended yellow color becoming terracotta with summer heat. 2. 'GRAtusc' exhibits a lower petal count. 3. 'GRAtusc' has mild sweet perfume whereas the seed parent has strong perfume with notes of citrus. The new rose plant 'GRAtusc' may be distinguished from its pollen parent, an unnamed breeding line, by the following combination of characteristics: 1. The flowers of 'GRAtusc' exhibit a distinct pink blended yellow color becoming terracotta with summer heat. 2. 'GRAtusc' has flowers that are not striped.

Comparisons with the most similar variety of common knowledge: Plants of the new cultivar 'GRAtusc' may be distinguished from the commercial variety *Rosa* hybrid 'RADrazz' (U.S. Pat. No. 11,836) by the following combination of characteristics: 1. The flowers of 'GRAtusc' exhibit a distinct pink blended yellow color becoming terracotta with summer heat whereas the flowers of 'RADrazz' are uniform dark pink to cerise. 2. Growth of 'GRAtusc' is upright to semi-weeping with bushy growth whereas 'RADrazz' growth is upright.

That which is claimed:

1. A new and distinct variety of *Rosa* hybrid plant named 'GRAtusc', as described and illustrated herein.

* * * * *